US00PP27166P3

(12) United States Plant Patent
Goffreda et al.

(10) Patent No.: US PP27,166 P3
(45) Date of Patent: Sep. 20, 2016

(54) APRICOT TREE NAMED 'NJA152'

(50) Latin Name: ***Prunus armeniaca* L.**
Varietal Denomination: NJA152

(71) Applicant: Rutgers, The State University, New Brunswick, NJ (US)

(72) Inventors: Joseph C. Goffreda, Millstone Township, NJ (US); Anna M. Voordeckers, East Windsor Township, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 229 days.

(21) Appl. No.: 13/999,233

(22) Filed: Jan. 31, 2014

(65) Prior Publication Data

US 2015/0223377 P1 Aug. 6, 2015

(51) Int. Cl.
*A01H 5/08* (2006.01)

(52) U.S. Cl.
USPC ..... Plt./186

(58) Field of Classification Search
USPC ..... Plt./156, 186
See application file for complete search history.

(56) References Cited

PUBLICATIONS

International Union for the Protection of New Varieties of Plants. 2007. Test Guidelines: Apricot. http://www.upov.int/en/publications/tg_rom/tg_index.html (3 pages total—cover page, pp. 7 and 24 only).*

* cited by examiner

*Primary Examiner* — Susan McCormick Ewoldt
*Assistant Examiner* — Karen Redden
(74) *Attorney, Agent, or Firm* — James A. Lucas; Driggs, Hogg, Daugherty & Del Zoppo Co., LPA

(57) ABSTRACT

A new and distinct apricot variety of *Prunus armeniaca* named 'NJA152' is provided. This variety is distinguished from other apricot varieties by its unique combination of a slightly later blooming habit, good production of glossy glabrous fruit with a red blush over a yellow-orange ground color, freestone flesh which has a melting texture and is moderately juicy, and flavor that is sweet-tart and aromatic.

6 Drawing Sheets

Latin name of genus and species of the plant claimed: *Prunus armeniaca* L.

CROSS REFERENCE TO RELATED APLICATION

NONE

STATEMENT REGARDING FEDERALLY SPONSORED RESEARCH OR DEVELOPMENT

NONE

BACKGROUND OF THE INVENTION

The present invention relates to a new and distinct variety of apricot tree named 'NJA152'. Our new tree resulted from planting an open pollinated apricot seed from an unknown cultivar. The new variety differs from other apricot cultivars in that the fruit have glabrous skin and the tree tends to bloom later in the spring. The resulting tree was selected when growing in a cultivated area as the $1^{st}$ tree in the $82^{nd}$ row of Block D at a Research Center in Cream Ridge, N.J.

BRIEF SUMMARY OF THE INVENTION

The 'NJA152' variety is distinguished from other apricot varieties due to the following unique combination of characteristics:

Trees that tend to bloom slightly later in the spring, resulting in generally good production of fruit that ripens in early mid-season.

Glossy, glabrous fruit with a red blush over a yellow-orange ground color.

Nearly round to slightly oblong fruit that are slightly compressed.

Fruit that are above average in eating quality, with a distinctive aromatic flavor and high soluble solids.

The variety was asexually reproduced at said Research Center in Cream Ridge, N.J. Asexual reproduction of this new variety by budding onto Lovell rootstock (unpatented) shows that the foregoing characteristics are so reproduced.

The following detailed description concerns the original tree, 'NJA152'. The original tree and asexual progeny have been observed growing in a cultivated area at said Research Center in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to The 1996 Edition of The Royal Horticultural Society (R.H.S.) Colour Chart.

BRIEF DESCRIPTION OF THE DRAWINGS

This new variety is illustrated by the accompanying photographic drawings, depicting the apricot tree by the best possible color representation using color photography. The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

Figure 1:
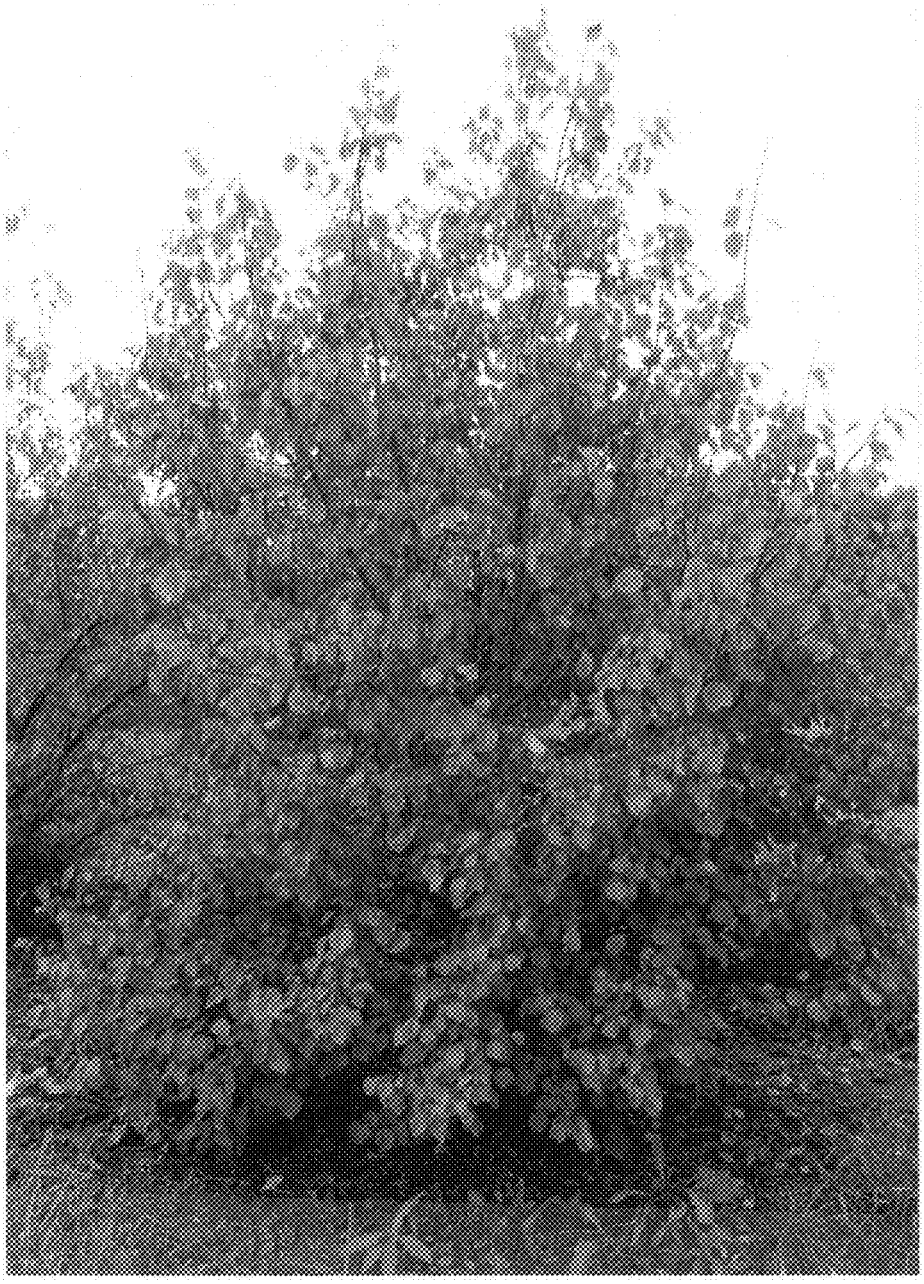
FIG. 1 is a color photograph of a tree of 'NJA152' in early fall that illustrates the moderately upright growth habit of a 5 year old tree at said Research Center in Cream Ridge, N.J. on Oct. 14, 2011.
Figure 2:
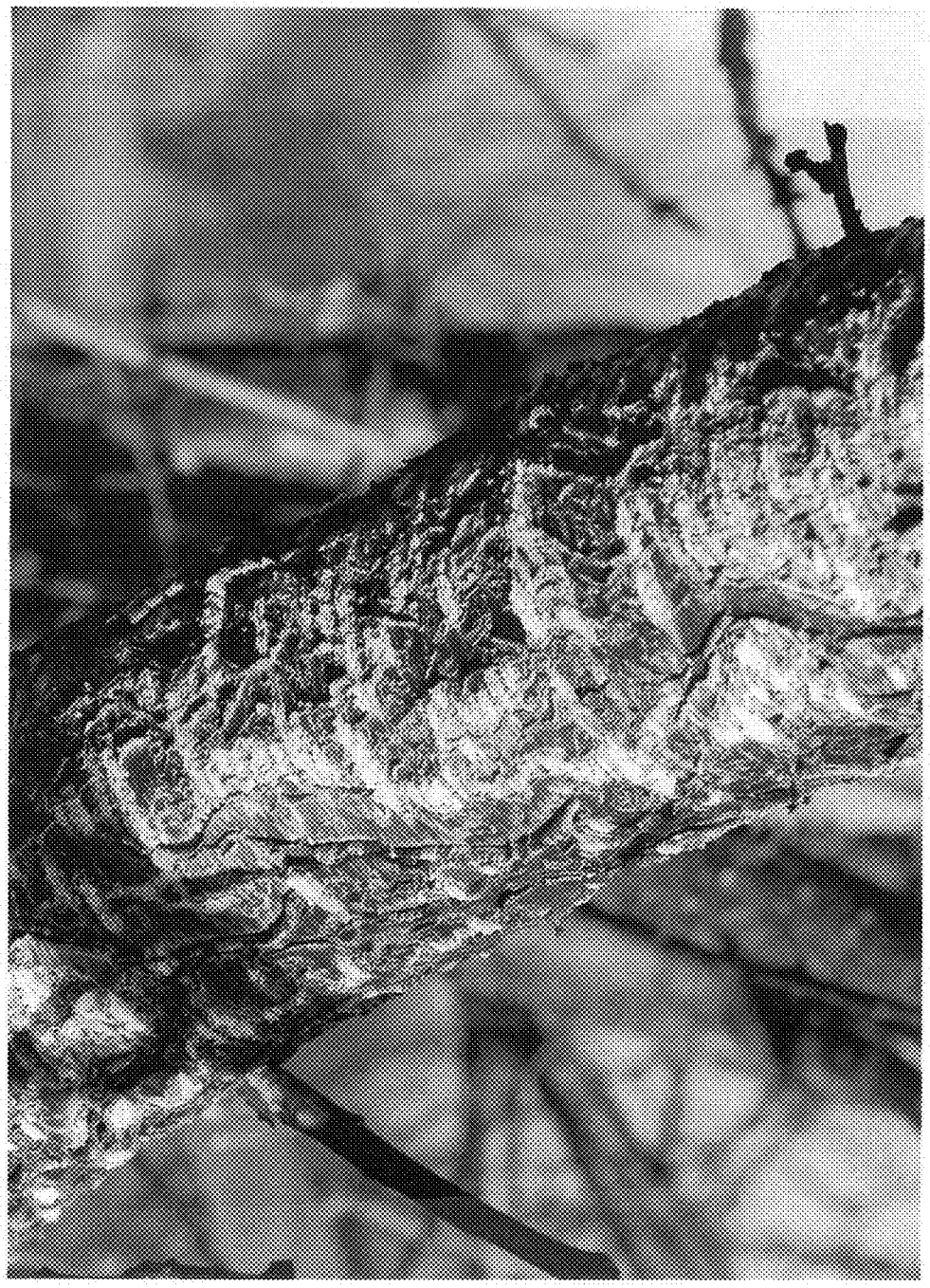
FIG. 2 is a color photograph taken on Jul. 2, 2013 of mature bark of 'NJA152' that illustrates the moderately rough texture of the mature bark.
Figure 3:
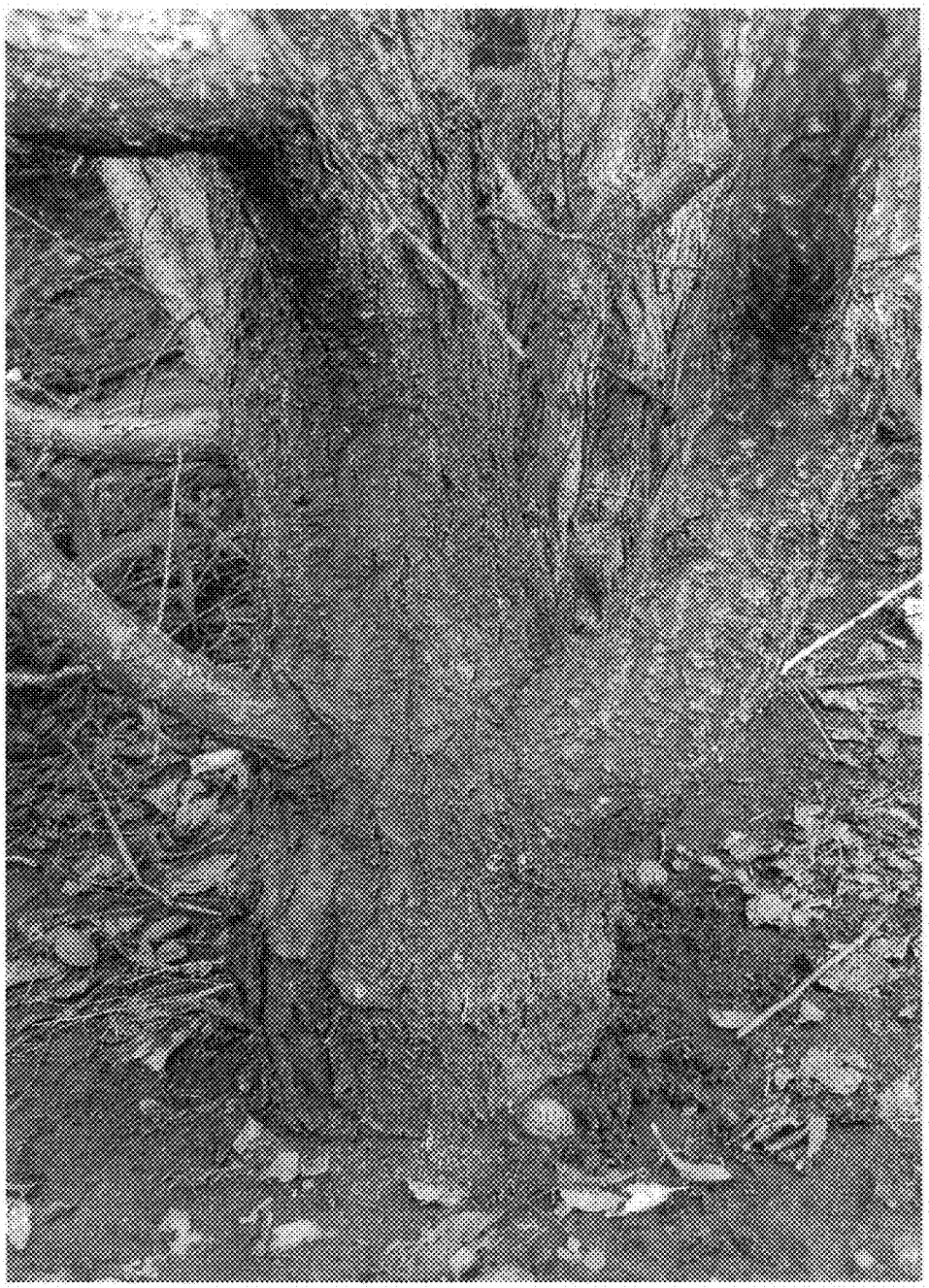
FIG. 3 is a color photograph taken on Dec. 3, 2013 of immature bark of 'NJA152' that illustrates color and density of elliptical greyed-orange lenticels on the immature bark.
Figure 4:
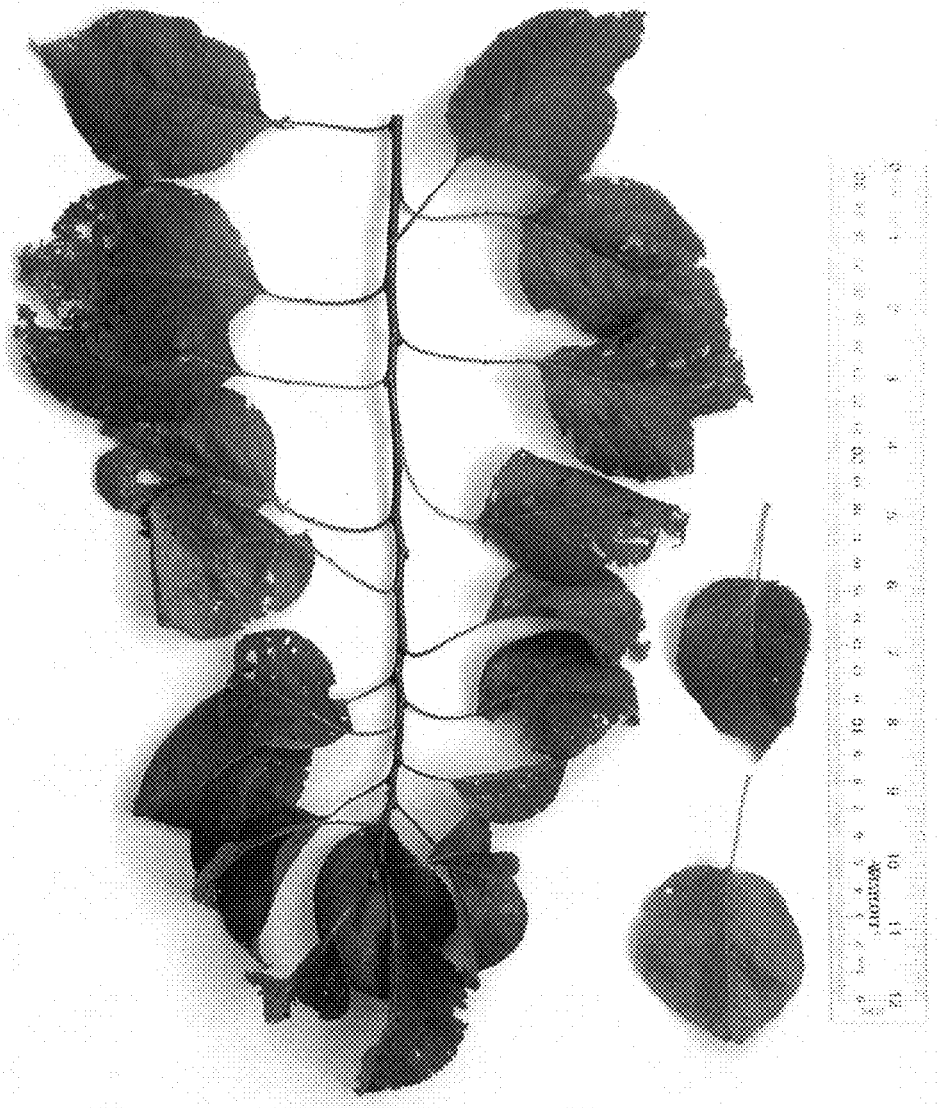
FIG. 4 is a color photograph taken on Aug. 16, 2013 of a characteristic twig of 'NJA152' in late summer bearing typical leaves of the mature foliage.
Figure 5:
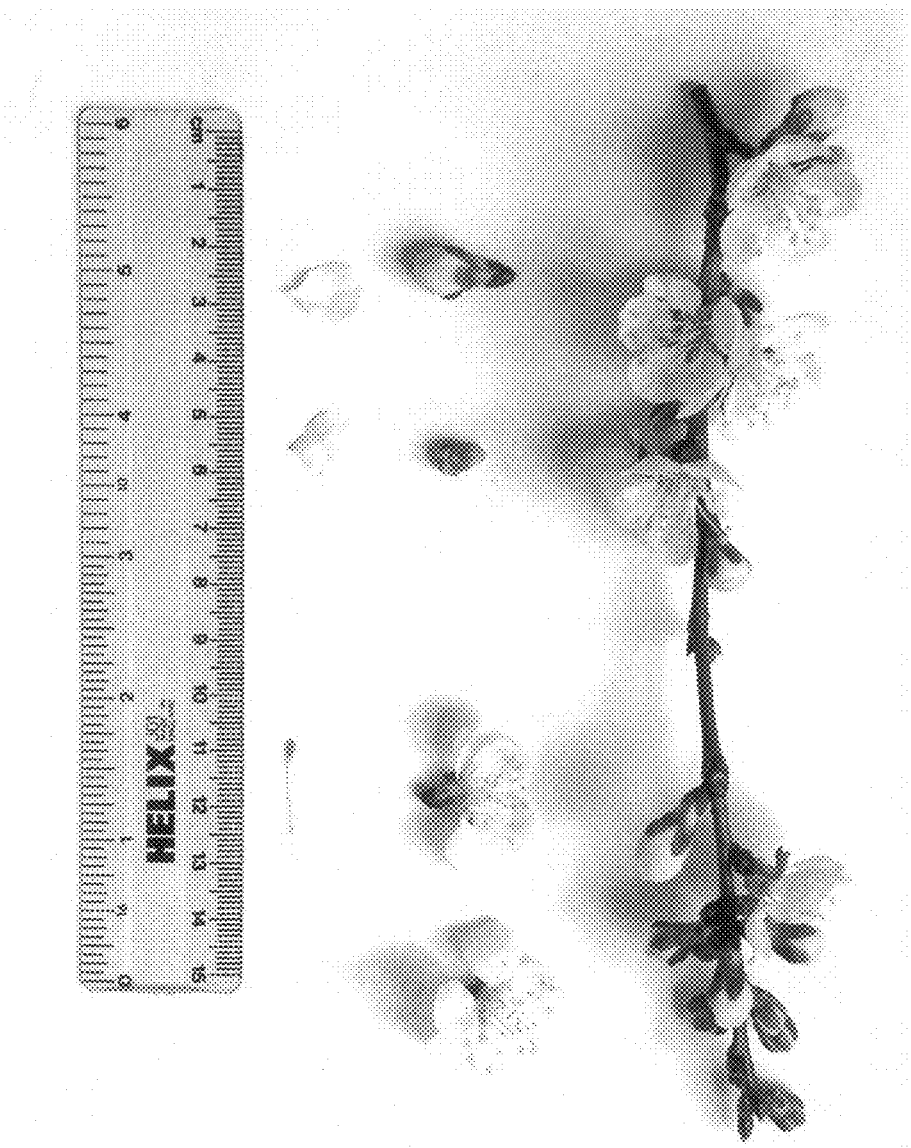
FIG. 5 is a color photograph taken on Mar. 20, 2012 of a characteristic twig of 'NJA152' that illustrates the typical flower buds and showy flowers of 'NJA152'.
Figure 6:
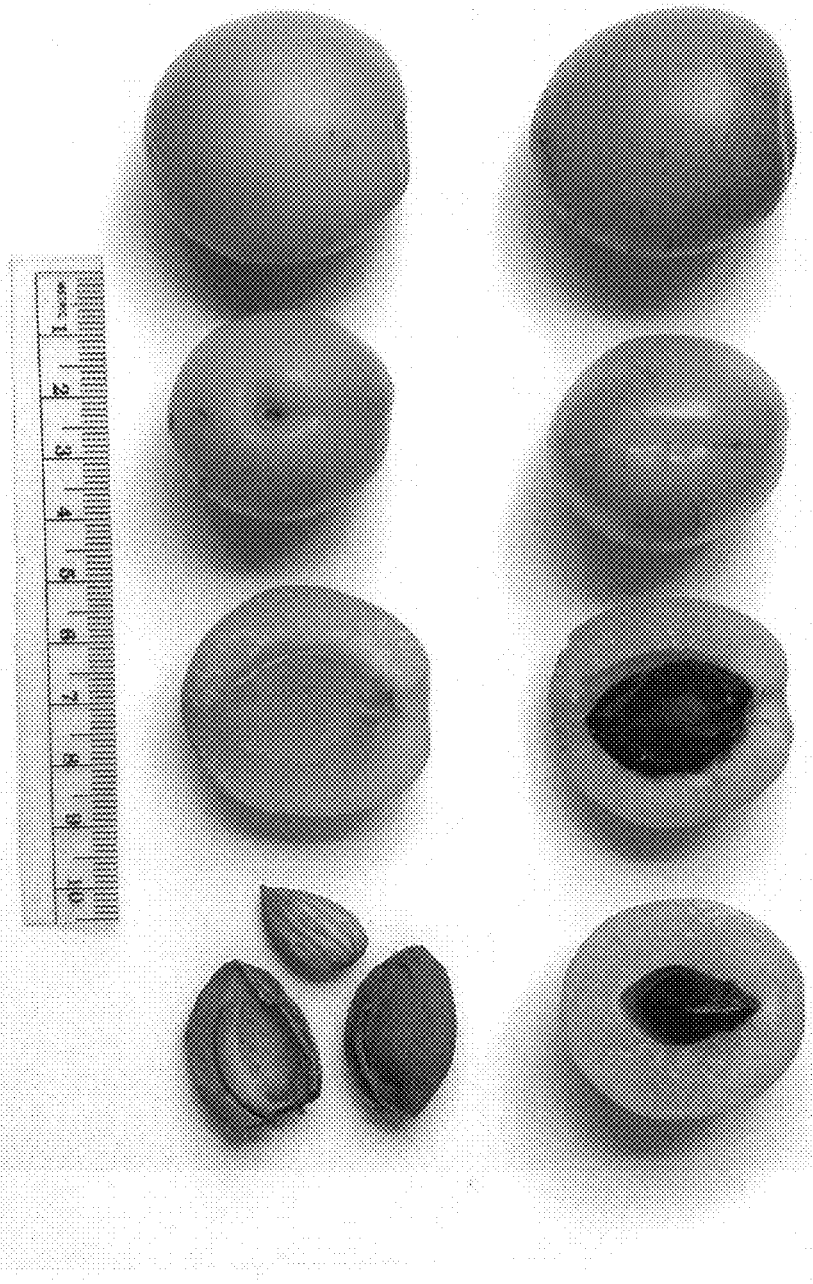
FIG. 6 is a color photograph taken on Jul. 3, 2013 of characteristic mature fruit, stones and fresh kernels of 'NJA152'. Whole fruit are presented in four positions and transverse and longitudinal sections to illustrate the yellow-orange flesh color and pericarp that does not adhere to the stone.

The following detailed description of the 'NJA152' variety is based on observations of a budded tree. The observed tree was 7 years of age and growing on 'Lovell' peach rootstock in Research Block C at the Research Center in Cream Ridge, N.J.

Scientific name: *Prunus armeniaca* L.

TABLE 1

| Parentage: | |
|---|---|
| Seed parent: | Unknown cultivar. |
| Pollen parent: | Open pollinated (pollen parent unknown). |

TABLE 2

| Tree: | |
|---|---|
| Vigor: | Moderately vigorous. |
| Plant hardiness zone: | Growth of plants has only been observed in zone 6b. |
| Dormant flower bud cold tolerance: | At least to −13° C. |
| Overall shape: | Upright to spreading. |
| Height: | Slightly below average as compared to other apricot cultivars. For example, measurement of a typical tree on 'Lovell' peach rootstock at seven years after planting shows an average height of 4 meters when grown in Cream Ridge, New Jersey. |
| Width: | Below average as compared to other apricot cultivars. For example, measurement of a typical tree on 'Lovell' peach rootstock at seven years after planting shows an average width of 3 meters when grown in Cream Ridge, New Jersey. |
| Caliper: | Seven year old tree is 24 cm in circumference measured at 5 cm from the ground. |

TABLE 3

| Trunk and branches: | |
|---|---|
| Trunk bark texture: | Moderately rough. |
| Trunk bark color: | Brown (RHS 200D). |
| Primary branches: | Branches that are approximately 15 cm in circumference are greyed-orange (RHS 176A) in color. |
| Lenticels: | Average density, approximately 1.1 per square cm; mostly elliptical in shape; typical examples of which measured 4.5 mm in length and 2.0 mm in width; orange-white (RHS 159A) in color. |
| Branch pubescence: | None. |
| New growth bark: | Greyed-orange (RHS 172A) in sun to greyed-orange (between RHS 166C and RHS 165B) in shade. |
| Internodes: | Length averaging 11.2 mm on a one-year shoot. |
| Degree of Branching | Medium |

TABLE 4

| Leaves: | |
|---|---|
| Texture: | Glabrous. |
| Sheen: | Mature leaves matte with a flat finish on the underside. |
| Length: | About 101 mm to 140 mm, averaging about 120 mm including the petiole. |
| Width: | About 62 mm to 76 mm, averaging about 67 mm. |
| Petiole: | About 42 mm in length and about 2 mm in diameter. |
| Margin. | Doubly serrate. |
| Margin undulation: | Nearly none. |
| Form: | Ovate. |
| Apex: | Cuspidate and curved downward. |
| Base: | Truncate. |
| Venation: | Pinnate. |
| Glands: | |
| Number: | About 1 to 6, averaging about 3.7. |
| Position: | Located on the petiole. |
| Size: | Averaging about 1 mm in both length and width. |
| Form: | Globose. |
| Stipules: | None observed on mature leaves. |
| Leaf Color: | |
| Upper leaf surface: | Yellow-green (RHS 146A). |
| Lower leaf surface: | Yellow-green (between RHS 146B and RHS 147C). |
| Vein: | Gteyed-yellow (RHS 160C). |
| Petiole: | Greyed-red (RHS 181A). |
| Pubescence: | None. |

TABLE 5

| Flowers: | |
|---|---|
| Size: | Medium size, typical flower measuring between 24.2 mm to 26.3 mm, averaging about 25.4 min across. |
| Color: | |
| Dormant bud: | Brown (between RHS 200A and RHS 200B). |
| Pink stage bud: | Red-purple (RHS 62C). |
| Open flower: | Young open flowers red-purple (RHS 65D) becoming red (RHS 36D) as they mature. |
| Distribution of flower buds | Distributed on both one year shoots and fruiting spurs, with a majority of crop borne on fruiting spurs |
| Petals: | Typically five petals per flower; cupped and round in shape; averaging about 13.9 mm long and 12.3 mm wide. Adaxial surface of the petals are red (RHS 36D) and abaxial surface is red-purple (RHS 65C), becoming red (RHS 36D) as they mature. |
| Petal apex: | Rounded. |
| Petal base: | Acute. |
| Stamens: | |
| Number: | Variable, 23 to 29, averaging about 26. |
| Length: | Variable, between 8.8 mm to 12.3 mm, averaging 10.7 mm. |

TABLE 5-continued

| Flowers: | |
|---|---|
| Filament color: | Green-white (RHS 157C). |
| Anther color: | Yellow (RHS 11A). |
| Pistil: | |
| Number: | One. |
| Size: | Length between 14.8 and 19.8 mm, averaging about 17.1 mm. |
| Pistil color: | Yellow-green (RHS 145C). |
| Ovary: | Ellipsoid in shape and not covered with any pubescence. |
| Sepals: | |
| Number: | Five. |
| Pubescence: | None. |
| Color: | Greyed-purple (RHS 183B). |
| Shape: | Triangular, with a rounded apex. |
| Size: | Length averaging 5.5 mm, width averaging 4.6 mm. |
| Nectar cup color: | Greyed-orange (RHS 163A). |
| Pollen: | Abundant; yellow (RHS 12B) in color. |
| Fragrance: | Slight to medium. |
| Bloom season: | Onset of bloom in 2011 on April 4; full bloom on April 7. |

TABLE 6

| Fruit: | |
|---|---|
| Size: | Small-medium, averaging about 4.3 cm long, 4.0 cm wide parallel to the suture and 3.7 cm wide perpendicular to the suture. |
| Typical weight: | 38 g. |
| Form: | |
| Longitudinal section: | Round, slightly oblong. |
| Traverse section: | Slightly elliptical. |
| Suture: | Shallow but distinct, extending from the base to apex. |
| Base: | Flat. |
| Apex: | Generally flat. |
| Stem: | Average length of 4.9 mm and an average diameter of 3.2 mm. |
| Skin: | |
| Thickness: | Above average. |
| Surface: | Glossy sheen, with no pubescence. |
| Tenacity: | Average. |
| Astringency: | None. |
| Tendency to crack: | Moderate if excessive rainfall during ripening. |
| Color: | Firm ripe fruit tend to have a red (between RHS 47A and RHS 47B) blush over a yellow-orange (RHS 20A) ground color, which may be yellow-green (RHS145B) at the suture. Ground color becomes yellow-orange (RHS 22A) when firm ripe. |
| Fruit Properties: | |
| Flesh color: | Yellow-orange (between RHS 23B and RHS 23C) which may be yellow-green (between RHS 145B and RHS 145C) at the suture. |
| Flesh firmness | Medium |
| Flesh adhesion: | |
| Juice: | Moderate. |
| Texture: | Melting. |
| Fibers: | Generally not noticeable. |

TABLE 6-continued

| Fruit: | |
|---|---|
| Stalk cavity depth | Medium |
| Picking Dates | First and last - June 28 and July 2 |
| Ripens: | Between June 30 and July 2 at Cream Ridge, New Jersey. |
| Flavor: | Above average, sweet-tart, and aromatic when soft ripe. |
| Soluble solids: | 20.8%. |
| Aroma: | High. |
| Eating quality: | Very good. |
| Keeping quality: | Average. Firmness and eating quality good for 7-10 days in cold (1° C.) storage, and 1-2 days at room temperature. |
| Shipping quality: | Average. |
| Usage: | Dessert. |
| Market: | Fresh market. |
| Productivity: | Good. Trees have produced a crop in 5 out of 7 years and a full crop in 3 out of 7 years at Cream Ridge, New Jersey when grown on non-dwarfing rootstock. Yields may be up to 1.5 tons per acre in fourth year to three tons or more pe racre in sixth and subsequent years. |

TABLE 7

| Stone: | |
|---|---|
| Type: | Freestone. |
| Form: | Ellipsoid. |
| Base angle: | Narrow. |
| Apex angle: | Medium. |
| Surface: | No prominent markings. |
| Ridge: | High flanked by shallow lines, extending from the base to the apex. |
| External color: | Greyed-orange (RHS 164B). |
| Internal color when cracked: | Greyed-orange (RHS 165C). |
| Cavity surface color: | Greyed-orange (RHS 165D). |
| Average stone dry weight: | 2.3 g. |
| Average stone wall thickness: | Varies between 2.6 and 4.1 mm. |
| Size: | Averages about 29.3 mm long, 19.4 mm wide parallel to the dorsal ridge, and 12.4 mm wide perpendicular to the dorsal ridge. |
| Tendency to split: | Low. |
| Kernel: | |
| Form: | Nearly elliptical. |
| Skin color: | Greyed-orange (RHS 165B). |
| Vein color: | Greyed-orange (between RHS 165A and RHS 165B). |
| Viability: | Yes. |
| Dry weight | 0.3 g. |
| Size: | Averages about 11.7 mm long, 8.6 mm wide, and 3.8 turn in breadth. |

Plant/fruit disease and pest resistance/susceptibility: No atypical resistances/susceptibilities have been noted under normal cultural practices.

We claim:

1. A new and distinct variety of apricot tree, substantially as herein shown and described.

* * * * *